(12) United States Patent
Wainer et al.

(10) Patent No.: US 6,387,268 B1
(45) Date of Patent: May 14, 2002

(54) IMMOBILIZATION OF MEMBRANE RECEPTOR ON HPLC

(75) Inventors: Irving Wainer; Yanxiao Zhang, both of Washington, DC (US)

(73) Assignee: Rett Corporation, Washington, DC (US)

(*) Notice: Subject to any disclaimer, the term of this patent is extended or adjusted under 35 U.S.C. 154(b) by 36 days.

(21) Appl. No.: 09/619,505

(22) Filed: Jul. 19, 2000

Related U.S. Application Data

(62) Division of application No. 09/255,881, filed on Feb. 23, 1999, now Pat. No. 6,139,735.
(60) Provisional application No. 60/075,745, filed on Feb. 23, 1998.

(51) Int. Cl.[7] .............................................. B01D 15/08
(52) U.S. Cl. .................... 210/635; 210/656; 210/198.2; 210/500.21; 210/500.27; 210/502.1
(58) Field of Search ................................ 210/635, 656, 210/659, 198.2, 500.21, 500.27, 502.1; 530/417

(56) References Cited

U.S. PATENT DOCUMENTS

| | | | | |
|---|---|---|---|---|
| 4,693,985 A | * | 9/1987 | Degen ..................... | 210/198.2 |
| 4,822,681 A | * | 4/1989 | Schossler ................ | 210/198.2 |
| 4,927,879 A | | 5/1990 | Pidgeon ..................... | 210/656 |
| 4,931,498 A | | 6/1990 | Pidgeon ..................... | 210/656 |
| 4,957,620 A | * | 9/1990 | Cussler .................... | 210/198.2 |
| 5,045,190 A | * | 9/1991 | Carbunell ................ | 210/198.2 |
| 5,149,425 A | * | 9/1992 | Mazid ..................... | 210/198.2 |
| 5,160,627 A | * | 11/1992 | Cussler .................... | 210/198.2 |
| 5,240,601 A | * | 8/1993 | Mazid ..................... | 210/198.2 |
| 5,240,856 A | * | 8/1993 | Goffe ...................... | 210/198.2 |
| 5,340,474 A | * | 8/1994 | Kauver ..................... | 210/198.2 |
| 5,529,686 A | * | 6/1996 | Hagen ..................... | 210/198.2 |

* cited by examiner

Primary Examiner—Ernest G. Therkorn
(74) Attorney, Agent, or Firm—Piper Marbury Rudnick & Wolfe LLP; Steven B. Kelber

(57) ABSTRACT

This invention provides a immobilized receptors on supports in liquid chromatographic systems. The method of the invention provides means of evaluating the attachment of agents to receptors comprising the steps of:

(a) immobilizing receptors on artificial membrane supports in a column,
(b) exposing the supports with the receptors to test agents at varying concentrations in a liquid chromatographic system,
(c) eluting the test agent from the column, and
(d) evaluating the elution profile of the test materials from the column.

Using this method, it is possible to evaluate the interaction of the test agent with the receptor. Following elution, it is possible to directly determine molecular structure by passing the elute through other testing devices such as a mass spectrometer.

13 Claims, No Drawings

IMMOBILIZATION OF MEMBRANE RECEPTOR ON HPLC

This application is a divisional, of application Ser. No. 09/255,881, filed Feb. 23, 1999, now U.S. Pat. No. 6,139,735 which takes priority from Provisional Application No. 60/075,745. filed Feb. 23, 1998.

FIELD OF THE INVENTION

This invention relates to immobilization of receptors on a support in a liquid chromatographic system.

BACKGROUND OF THE INVENTION

The combinatorial synthesis of chemical libraries has created an enormous pool of possible new drug candidates. Indeed, synthetic capabilities have outstripped the ability to determine corresponding biological activity. An initial step in the resolution of this problem has been the development of microtiter plates which contain immobilized receptors/ antibodies. The use of these plates can rapidly reduce the number of possible candidates in a combinatorial pool from thousands to hundreds. However, assignment of relative activity within the reduced pool of compounds remains a slow and repetitive process.

The relationship between basic pharmacological processes and liquid chromatographic (LC) studies have been emphasized by the inclusion of biomolecules as active components of chromatographic systems. A wide variety of immobilized biopolymer-based LC stationary phases (BP-SPs) have been developed using proteins, enzymes, cellulose and amylose, macrocyclic antibodies and liposomes. Indeed, it has been demonstrated that the chromatographic retention and selectivity of BP-SPs are related to the properties of the non-immobilized biopolymer. For example, retention of a compound on an SP column containing immobilized human serum albumin has been used to evaluate the binding properties of the compounds to proteins.

SUMMARY OF THE INVENTION

This invention provides a immobilized receptors on supports in liquid chromatographic systems. Using the methods of the invention, it is possible to immobilize receptors on supports, then expose those receptors to agents that might attach to the receptors. It is then possible to expose the supports with the receptors, followed by liquid chromatographic studies to determine whether attachment of the agent to the receptor has occurred. It is, of course, also possible to expose the receptors on the supports to substances that might inhibit interaction between the agent that is known to interact with the receptor, then expose the supports with the receptors to the agent to determine whether or not the proposed inhibitor will, in fact, inhibit attachment to the receptor. Hence, using means of the invention, it is possible to test interaction of potential drugs and receptors and also to evaluate possible agents for inhibition of receptor interactions.

DESCRIPTION OF THE INVENTION

It is the purpose of this invention to provide means for immobilization of membrane receptors in order to study relative a ligand-receptor interactions utilizing LC techniques. This method has been tested using neuronal nicotinic acetylcholine receptors as an example. The fundamental processes of drug action, absorption, distribution and receptor activation, are dynamic in nature and have much in common with the basic mechanisms involved in chromatographic distribution. Indeed, the same basic intermolecular interactions (hydrophobic, electrostatic and hydrogen bonding) determine the behavior of chemical compounds in both biological and chromatographic environments.

Although membrane receptors play an important role in drug activity and are key targets in combinatorial screens, they have not been included in LC systems. This has been due, in part, to the disruption of the tertiary structure of the receptor produced by covalent immobilization on a solid LC support. One solution to this problem is the immobilization of membrane receptors in the phospholipid monolayer of an immobilized artificial membrane (IAM) LC stationary phase.

The method provides means of evaluating the attachment of agents to receptors comprising the steps of:
(a) immobilizing receptors on artificial membrane supports in a column,
(b) exposing the supports with the receptors to test agents at varying concentrations in a liquid chromatographic system,
(c) eluting the test agent from the column, and
(d) evaluating the elution profile of the test materials from the column.

Using this method, it is possible to evaluate the interaction of the test agent with the receptor. Following elution, it is possible to directly determine molecular structure by passing the elute through other testing devices such as a mass spectrometer.

In the examples, the IAM LC stationary phase is derived from the covalent immobilization of 1-myristoyl-2-[(13-carboxyl)tridecanoyl]-sn-3-glycerophosphocholine on aminopropyl silica and resembles ½ of a cellular membrane. In the IAM phase, the phosphatidylcholine headgroups form the surface of the support and the hydrocarbon side chains produce a hydrophobic interphase which extends from the charged headgroup to the surface of the silica. (This phase has been previously used to immobilize hydrolytic and cofactor-dependent enzymes without loss of activity.)

Nicotinic acetylcholine receptors (nAChRs) are ligand-gated ion channels formed from five homologous subunits oriented like barrel staves center pore. The nAChRs are the primary excitatory neurotransmitter receptors on skeletal muscles and autonomic ganglia in the peripheral nervous system of vertebrates. In the central nervous system, the nAChRs play important roles in modulating functions of other neurotransmitters. Sixteen different subunits of nAChRs have been identified so far. These subunits combine to form a variety of nAChR subtypes. A stably transfected mammalian cell line established recently expresses a single subtype of rat nAchRs, $\alpha 3/\beta 4$, at a level that is at least 30 times higher than the expression level of native nAChRs in mammalian tissue. The rat $\alpha 3\beta 4$ nAChR, therefore, was selected for the initial development of a receptor-bearing LC stationary phase.

The $\alpha 3/\beta 4$ nAChRs prepared from the cell line were solubilized using a detergent solution. The resulting detergent-receptor solution was mixed with the dry IAM LC support and then dialyzed against Tris-HCl buffer [50 mM, pH 7.4]. Additional buffer was added to the IAM support and the mixture was vortexed, centrifuged and the supernatant decanted. The resulting IAM LC support contained approximately 60 mg protein per gram IAM support.

The ability of the immobilized receptors to bind known nAChR ligands was determined using a [$^3$H]epibatidine binding assay protocol designed for cell membrane homogenates. In the binding assays, the α3/β4 IAM support suspension showed 98% specific binding with 5 ηM active receptor per gram immobilized protein, comparable to 100% specific binding with 8.6 ηM per gram protein found in parallel experiments for the receptor-detergent solution. No specific binding was found to the native IAM LC support.

Materials and Methods

Immobilization of Receptor on the Chromatopraphic Matrices

The cultured cells in which rat α3/β4 subtype of neural nicotinic acetylcholine receptor (nAChR) were expressed by transfected cell line KXα3β4R$_2$ were harvested in 30 ml of Tris-HCl buffer (50 mM, pH 7.4) and homogenized for 20 minutes with a Brinkman Polytron homogenizer. The homogenates were centrifuged at 35,000×g for 10 minutes and the supernatant was discarded. The resulting pellets were suspended in 6 ml of 2% cholate in Tris-HCl buffer (50 mM, pH 7.4) and stirred for two hours in an ice bath. After centrifugation at 35,000×g, the supernatant was collected for the immobilization. IAM packing materials (200 mg) were washed three times by centrifugation with Tris-HCl buffer (50 mM, pH 7.4). The IAM materials were suspended in 4 ml of receptor-detergent solution, stirred for one hour at room temperature and dialyzed against 2×1 L buffer for 24 hours at 4° C. When detergents were depleted from the mixture, the receptors were hydrophobically entrapped in the phospholipid monolayer on the surface of IAM materials. The receptor-IAM materials were washed with buffer by centrifugation at 4000×g.

Frontal Chromatography Using Immobilized NR(α4β2)-IAM

The NR(α4β2)-IAM packing materials were packed in an HR glass column (Pharmacia Biotech) and connected with an HPLC pump. 15–20 ml of [$^3$H]-EB in buffer or in the same buffer containing drugs was applied by a 25 ml sample superloop (Pharmacia Biotech, Uppsala, Sweden) and run at a flow rate of 0.4 ml/min at room temperature. The elution profile was monitored by an on-line radioactivity HPLC detector.

EXAMPLE 1

A 0.5×1.25 cm LC column with a 0.245 ml bed volume was packed with the (α3/β4) NR-IAM material. The resulting column was used in the LC study of drug-NR binding using frontal chromatographic techniques with [$^3$H]-epibatidine (EB) as the marker ligand. A series of [$^3$H]-EB concentrations ranging from 60 pM to 600 pM were pumped through the (α3/β4)NR-IAM column2 to obtain elution profiles showing front and plateau regions. The concentration of the [$^3$H]-EB in the column eluent was monitored by an LC on-line radioactivity detector. The retention volumes of [$^3$H]-EB was increased to 600 pM.

EXAMPLE 2

The binding of the [$^3$H]-EB on the (α3/β4)NR-IAM column was be altered by the addition of competitive NR-ligands to the mobile phase. The retention volume of 60 pM [$^3$H]-EB (60 pM) was decreased from 9.5 to 6.6 ml when a 10 nM concentration of the NR-ligand A85380 was added to the mobile phase and fell to 1.9 ml when the A85380 concentration was increased to 100 nM.

Using the techniques of the invention, the relative affinities of ligands for the receptors can be readily classified by determining the concentrations required to decrease the retention volumes of [$^3$H]-EB to a predetermined level. For example, to decrease the retention volumes of 60 pM [$^3$H]-EB from 9.5 ml to 6 ml required mobile phase concentration of 120 pM of (±)-EB, 17 mM of A85380, 45 nM of nicotine, 1.3 μM of carbachol and 21 μM of atropine, respectively. The relative affinities for the NR determined by this method were (±)-EB>A85380>nicotine>carbachol>atropine, which is consistent with results from standard by binding assays.

Frontal chromatography can be used to calculate dissociation constants, $K_d$, for the marker and displace ligands. In the data collected, the mobile phase concentrations of [$^3$H]-EB and the competitive ligands were varied and association constant of EB, $K_{EB}$ and the test ligands, $K_{drug}$, as well as the number of the active and available binding sites of immobilized receptors, P, were calculated using equations 1 and 2

$$(V_{max}-V)^{-1}=(1+[EB]K_{EB})(V_{min}[EB]K_{EB})^{-1}+(1+[EB]K_{EB}^{-2}(V_{min}[EB]D_{EB}K_{drug})^{-1}[\text{drug}]^{-1} \quad (1)$$

$$(V-V_{min})^{-1}=(V_{min}[P]V_{EB})^{-1}+(V_{ml}[P]^{-1}[EB] \quad (2)$$

where V is the retention volume of EB; $V_{max}$ is the retention volume of EB at low concentration (60 pM) and in the absence of drugs, $V_{min}$ is the retention volume of EB when the specific interaction is completely suppressed. $V_{min}$ was determined by running [$^3$H]-EB in a series of concentration of drugs and plotting $1/(V_{max}-V)$ versus 1/[drug] extrapolating to finite [drug].

Using methods of the invention, the supports with the receptors may be exposed to drugs or inhibitors, then to drugs followed by chromatographic evaluation of the presence of the drug by chromatographic means to determine whether the drug is present on the support. Using means of the invention, it would also be possible to determine whether proposed inhibitors of receptor/toxin interaction will, in fact, prevent that interaction by exposing the support with receptors bound thereto to proposed inhibitors, then to the toxin or drug followed by chromatographic evaluation of the support to determine whether the toxin or drug has been prevented from binding to the receptor by the inhibitor under consideration.

While the invention has been exemplified using certain rat brain receptors, any receptor system may be used. Other receptors such as GABA receptors have been tested and found to function in a manner similar to those exemplified herein. Examples of other receptors include, steroid receptors such as estrogen based receptors or non-estrogen based receptors that may be turned on by compounds with estrogenic properties would be appropriate for use in the methods of the invention. Androgen receptors could be used to detect possible androgenic activity of substances.

Other supports than those exemplified which are HPLC-type supports known in the art may be used. Supports such as hydrogel beads or hydrophilic verticle support systems may be used in the methods of the invention.

Because the methods of the invention require only evaluation of comparative elution volume profiles with the test material being fully eluted at the end of the study, the receptor binding column can be reused repeatedly

What we claim is:

1. A method of identifying whether a compound is a specific ligand for at least one cellular receptor comprising (1) contacting an artificial membrane support having non-covalently immobilized thereon, said at least one cellular receptor to a liquid flow system comprising said compound, and (2) determining whether said compound becomes specifically bound to said support wherein said cellular receptor is immobilized such that its conformational structure after immobilization permits specific binding to ligands that are bound by said at least one cellular receptor when it is comprised in its native cellular environment, said artificial membrane support is contained in a liquid flow system; and said artificial membrane support is produced by the following steps:
  (i) obtaining an immobilized artificial membrane (IAM) liquid chromatographic (LC) stationary phase comprising a phospholipid monolayer;
  (ii) contacting said IAM LC stationary phase with at least one solubilized receptor or receptor-ligand output under conditions wherein that at least one solubilized receptor or receptor-ligand output becomes non-covalently immobilized in the phospholipid monolayer of said IAM LC stationary phase such that the tertiary structure of said at least one immobilized cellular receptor permits specific binding to ligands that are bound by said at least one cellular receptor when it is comprised in its native cellular environment; and
  (iii) contacting said artificial membrane support comprising at least one non-covalent immobilized cellular receptor to a liquid flow system.

2. The method of claim 1, which further comprises contacting said artificial membrane support to a liquid flow system containing a second compound that putatively affects binding of said first compound to said at least one immobilized cellular receptor; and
  determining whether said compound affects the binding of said first compound to said artificial membrane support.

3. The method of claim 2, which is used to identify a compound that inhibits the binding of a neurotransmission receptor or a steroid receptor to a ligand that specifically binds to said receptor.

4. The method of claim 3, wherein said receptor is a GABA receptor, nicotinic acetylcholine receptor, estrogen receptor or androgen receptor.

5. The method of claim 2, wherein said second compound inhibits the binding of said immobilized receptor to said first compound.

6. The method of claim 1, wherein said compound is a drug or toxin.

7. The method of claim 1, which is used to identify compounds that bind to a receptor involved in neurotransmission or a steroid receptor.

8. The method of claim 7, wherein said receptor is a GABA receptor, nicotinic acetylcholine receptor, estrogen receptor, or androgen receptor.

9. A method for identifying, purifying or isolating a compound that affects the binding of a ligand to a cellular receptor that is specifically bound by said ligand comprising:
  (i) contacting an artificial membrane support having non-covalently immobilized thereon at least one cellular receptor and to which at least one cellular receptor is itself specifically bound to a ligand to a liquid flow system that contains at least one compound that potentially affects the binding of said ligand which is specifically bound to said non-covalently immobilized cellular receptor;
  (ii) identifying, purifying or isolating said at least one compound based on its ability to affect the binding of said ligand to said immobilized cellular receptor; wherein said immobilized cellular receptor is immobilized to said artificial membrane support such that after immobilization specifically binds to ligands that are bound by said at least one cellular receptor when it is comprised in its native cellular environment, and wherein said artificial membrane support is contained in a liquid flow system; and further wherein said artificial membrane support is produced by the following steps:
    (1) obtaining an immobilized artificial membrane (IAM) liquid chromatographic (LC) stationary phase comprising a phospholipid monolayer;
    (2) contacting said IAM LC stationary phase with at least one solubilized receptor or solubilized receptor-ligand complex under conditions wherein that at least one solubilized receptor or solubilized receptor-ligand complex becomes non-covalently immobilized in the phospholipid monolayer of said IAM LC stationary phase such that at least one immobilized cellular receptor permits specific binding to ligands that are bound by said at least one cellular receptor when it is comprised in its native cellular environment; and
    (3) optionally contacting said artificial membrane support to which is immobilized at least one cellular receptor with at least one ligand that specifically binds said at least one immobilized receptor under conditions that result in said ligand becoming specifically bound to said at least one cellular receptor non-covalently immobilized to said support.

10. The method of claim 9, wherein said compound competes with said ligand for binding to said immobilized cellular receptor.

11. The method of claim 9, wherein said compound is obtained from a combinatorial chemical library of potential drug candidates.

12. The method of claim 9, wherein said compound is contacted with said artificial membrane support comprising said immobilized receptor/ligand complex by use of a liquid chromatographic system that comprises varying concentrations of said compound.

13. The method of claim 12, wherein the compound becomes specifically bound to the support and the elution profin of said compound is evaluated upon eluting said compound from the support.

* * * * *